(12) United States Patent
Kirenko et al.

(10) Patent No.: US 9,265,456 B2
(45) Date of Patent: Feb. 23, 2016

(54) DEVICE AND METHOD FOR DETERMINING VITAL SIGNS OF A SUBJECT

(71) Applicant: KONINKLIJKE PHILIPS N.V., Eindhoven (NL)

(72) Inventors: Ihor Olehovych Kirenko, Eindhoven (NL); Willem Verkruijsse, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 157 days.

(21) Appl. No.: 14/207,785

(22) Filed: Mar. 13, 2014

(65) Prior Publication Data

US 2014/0276089 A1    Sep. 18, 2014

Related U.S. Application Data

(60) Provisional application No. 61/781,269, filed on Mar. 14, 2013, provisional application No. 61/844,453, filed on Jul. 10, 2013.

(30) Foreign Application Priority Data

Mar. 14, 2013  (EP) .................................... 13159173
Jul. 10, 2013   (EP) .................................... 13175914

(51) Int. Cl.
*A61B 5/024*  (2006.01)
*A61B 5/1455* (2006.01)
(Continued)

(52) U.S. Cl.
CPC ........... *A61B 5/14551* (2013.01); *A61B 5/0077* (2013.01); *A61B 5/01* (2013.01); *A61B 5/0295* (2013.01); *A61B 5/02416* (2013.01); *A61B 5/0816* (2013.01); *A61B 5/7278* (2013.01)

(58) Field of Classification Search
None
See application file for complete search history.

(56) References Cited

U.S. PATENT DOCUMENTS 8,634,591 B2     1/2014  Jeanne et al.
2009/0141124 A1  6/2009  Liu et al.
(Continued)

FOREIGN PATENT DOCUMENTS

| EP | 2546780 A1 | 1/2013 |
|---|---|---|
| WO | 2010001248 A2 | 1/2010 |
| WO | 2013027027 A2 | 2/2013 |

OTHER PUBLICATIONS

Karlen, W., et al.; Photoplethysmogram signal quality estimation using repeated Gaussian filters and cross-correlation; 2012; Physiological Measurement; 33(10)1617-1629.

(Continued)

*Primary Examiner* — Siamak Harandi

(57) ABSTRACT

A device for determining a vital sign of a subject comprises an interface for receiving a data stream derived from detected electromagnetic radiation reflected from a region of interest including a skin area of the subject, said data stream comprising a data signal per skin pixel area of one or more skin pixels for a plurality of skin pixel areas of said region of interest, a data signal representing the detected electromagnetic radiation reflected from the respective skin pixel area over time. An analyzer is provided for analyzing spatial and/or optical properties of one or more data signals in one or more wavelength ranges. A processor is provided for determining a vital sign information signal of the subject based on the data signals of skin pixel areas within the skin area, and a post-processor is provided for determining the desired vital sign from said vital sign information signal. The determined spatial and/or optical properties are used by the processor for determining the vital sign information signal and/or by the post-processor for determining the desired vital sign.

18 Claims, 3 Drawing Sheets

(51) Int. Cl.
    *A61B 5/01*         (2006.01)
    *A61B 5/0295*     (2006.01)
    *A61B 5/08*         (2006.01)
    *A61B 5/00*         (2006.01)

(56) References Cited

U.S. PATENT DOCUMENTS

2009/0226071 A1*   9/2009   Schuler et al. ................ 382/133
2011/0311143 A1    12/2011   Cennini et al.
2012/0179011 A1*   7/2012   Moon et al. .................... 600/324
2012/0203080 A1    8/2012   Kim et al.

OTHER PUBLICATIONS

Singh, M., et al.; Spatial texture analysis: a comparative study; 2002; Pattern Recognition; vol. 1; pp. 676-679.

Tsouri, G. R., et a.; Constrained independent component analysis approach to nonobtrusive pulse rate measurements; 2012; Journal of Biomedical Optics; 17(7)077011-1.

Verkruysse, W., et al.; Remote plethysmographic imaging using ambient light; 2008; Optical Express; 16(26) 21434-21445.

Wieringa, F. P., et al.; Contactless Multiple Wavelength Photoplethysmographic Imaging: A First Step Toward "SpO2 Camera" Technology; 2005; Annals of Biomedical Engineering; 33(8)1034-1041.

Lewandowska, M., et al.; Measuring Pulse Rate with a Webcam-a Non-contact Method for Evaluating Cardiac Activity; 2011; IEEE Trans. on Proc. of Fed. Conf. on Computer Science and Information Systems; pp. 405-410.

MIT; Your Vital Signs, on Camera; 2010; MIT News Office; downloaded Mar. 28, 2013. web.mit.edu/newsoffice/2010/pulse-camera-1004.html.

Poh, M-Z, et al.; Advancements in Noncontact, Multiparameter Physiological Measurements Using a Webcam; 2011; IEEE Trans. on Biomedical Engineering; 58(1)7-11.

\* cited by examiner

DEVICE AND METHOD FOR DETERMINING VITAL SIGNS OF A SUBJECT

CROSS REFERENCE TO RELATED APPLICATIONS

This application claims the benefit of U.S. provisional application Ser. No. 61/781,269 filed Mar. 14, 2013 and European provisional application serial no. 13,159,173.7 filed Mar. 14, 2013 and U. S. provisional application Ser. No. 61/844,453 filed Jul. 10, 2013 and European provisional application Ser. No. 13175914.4 filed Jul. 10, 2013, all of which are incorporated herein by reference.

FIELD OF THE INVENTION

The present invention relates to a device and a method for determining the vital signs of a subject. In particular, the present invention relates to an unobtrusive optical measurement approach which can be used for detecting vital signs in an observed subject, such as a person or animal. In this context, optical measurement refers to remote photoplethysmography (R-PPG).

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heartbeat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the (arterial) blood oxygen saturation (also called SpO2) of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG (R-PPG) devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16 (26), 22 Dec. 2008, pp. 21434-21445 demonstrates that photoplethysmographic signals can be measured remotely using ambient light and a conventional consumer level video camera.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using remote PPG technology, vital signs can be measured from video camera signals providing a time sequence of image frames, as it is revealed by minute light absorption changes in the skin caused by the pulsating blood volume. As this signal is very small and hidden in much larger variations due to illumination changes and motion, there is a general interest in improving the fundamentally low signal-to-noise ratio (SNR). There still are demanding situations, with severe motion, challenging environmengtal illumination conditions, or high required accuracy of the application, where an improved robustness of the remote PPG devices and methods are required. For instance, it is a particular challenge to reliably differentiate a pulse signal with low SNR from other periodic signal acquired by the same imaging unit (camera). Those noisy signals might have an amplitude and frequency in the same range as a heartbeat signal, and therefore might be confused with the real heartbeat signal.

When applying the R-PPG technology in healthcare applications, such situations with misdetection of a real heartbeat signal and its confusion with a noise could lead to serious problems. For instance, a rapid deterioration of a health condition of a person might be left unnoticed due to misdetection of a weak pulse signal. Therefore, there is a need for a method for reliable discrimination of a pulse signal from other noise signals with similar temporal and frequency characteristics during HR monitoring with R-PPG camera-based technology.

SUMMARY OF THE INVENTION

It an object of the present invention to provide an improved device and method for determining vital signs of a subject having an increased signal-to-noise ratio and particularly allowing to reliably distinguish between a heart rate signal from other noise signals having similar temporal and frequency characteristics.

In a first aspect of the present invention a device for determining vital signs of a subject is presented, the device comprising:

an interface configured to receive a data stream derived from detected electromagnetic radiation reflected from a region of interest including a skin area of the subject, said data stream comprising a data signal per skin pixel area of one or more skin pixels for a plurality of skin pixel areas of said region of interest, a data signal representing the detected electromagnetic radiation reflected from the respective skin pixel area over time, an analyzer configured to analyze spatial and/or optical properties of one or more data signals in one or more wavelength ranges, a processor configured to determine a vital sign information signal of the subject based on the data signals of skin pixel areas within the skin area, and a post-processor configured to determine the desired vital sign from said vital sign information signal, wherein said determined spatial and/or optical properties are used by the processor for determining the vital sign information signal and/or by the post-processor for determining the desired vital sign.

In a further aspect of the present invention a corresponding method for determining vital signs of a subject is presented.

In still a further aspect of the present invention a system for determining vital signs of a subject is presented, said system comprising:

an imaging unit for detecting electromagnetic radiation reflected from a region of interest including a skin area of the subject to obtain a data stream, said data stream comprising a data signal per skin pixel area of one or more skin pixels for a plurality of skin pixel areas of said region of interest, a data signal representing the detected electromagnetic radiation reflected from the respective skin pixel area over time, and a device for receiving said data stream and for determining a vital sign of a subject from said data stream.

In yet further aspects of the present invention, there are provided a computer program which comprises program code means for causing a computer to perform the steps of the method when said computer program is carried out on a computer as well as a non-transitory computer-readable recording medium that stores therein a computer program product, which, when executed by a computer processor, causes the method disclosed herein to be performed.

Preferred embodiments of the invention are defined in the dependent claims. It shall be understood that the claimed method, system, computer program and medium have similar and/or identical preferred embodiments as the claimed device and as defined in the dependent claims.

Many known methods and devices for camera-based HR detection are based on the assumption that a pulse signal is the only periodic signal detected by a camera, while noise (e.g. induced by motion or illumination changes) is substantially a non-periodic signal. Sometimes, differentiation between a real pulse signal and noise is done based on amplitude analysis (heartbeat signal is expected in a certain amplitude range). Moreover, the assumption is usually made that a heartbeat signal is always present in monitored subject, and then an algorithm should just find a periodic signal, which would be a heartbeat. It has, however, been found that such assumptions are not always valid in "real-life" situations. An unhealthy subject might have non-periodic HR, or fast changing HR. Moreover, the noise might have temporal and frequency characteristics in the range of those of the real pulse signal. For instance, flickering ambient illumination might introduce a periodic component in the acquired PPG signal, which might have a more stable frequency than a heart rate.

Thus, the device and method proposed by the present invention does not rely on one-dimensional characteristics of the acquired signal to distinguish a real pulse signal from noise with similar temporal characteristics, but on optical and spatial properties of the remote PPG signal, i.e. the data signals contained in the data stream output by an imaging unit in response to received electromagnetic radiation (e.g. acquired image frames of the subject).

The proposed device and method are particularly based on the processing of a data stream (such as a video from a camera with at least two color channels (e.g. R and G channels of an RGB camera) to differentiate a real PPG signal from other repetitive signals with frequencies and amplitude range similar to PPG signal. To distinguish a real pulse signal from a noise signal spatial and/or optical properties of the PPG signal (one or more data signals) are analyzed. Spatial properties are e.g. used in an analysis of the distribution of the PPG signal amplitude over one or more skin pixel areas (i.e. one or more areas of the skin area of the subject). Optical properties are e.g. used in an analysis of one or more of the ratio of PPG signal amplitudes in color channels (wavelength ranges) depending on a wavelength, the distribution of the maximum range of amplitudes of PPG signals in various color channels and/or temporal stability of amplitudes of PPG signals in various color channels.

The result of the analysis, i.e. the determined information about the temporal and/or spatial properties of the one or more data signals in the one or more wavelength ranges, is primarily used to determine if a data signal contains or is usable to derive a vital sign information signal of the subject or if it is a noisy signal falsifying or even making it impossible to reliably derive a vital signal information signal there from.

Furthermore, it may be used to adjust one or more parameters and/or an algorithm used for extraction and/or post-processing, in particular for determining the vital sign information signal, for determining the desired vital sign and/or for determining parameters of an imaging unit used for acquisition of electromagnetic information, Still further, it may be used to select an optimal size and shape of the ROI on a skin for acquisition of vital signs or to select a post-processing method which is the most optimal for the determined spatial and/or temporal properties of the skin area. Thus, the signal-to-noise ratio and the efficiency in reduction of artifacts caused by motion of a subject or illumination changes can be efficiently improved.

Apart from detecting heart rate signals (and distinguishing from noise) the invention can be used also for extraction of other vital signs derived from PPG information. For instance, SpO2 calculation can be applied to a (component of) signal in the red (R) channel after validation that that signal is truly a PPG signal and not noise.

The interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e.

a living being) and derivative parameters. In particular, the term "vital sign" comprises heart rate (HR) (sometimes also called pulse rate), heart rate variability (pulse rate variability), pulsatility strength, perfusion, perfusion variability, PPG pulsatility, Traube Hering Mayer waves, respiratory rate (RR), body skin temperature, blood pressure, pulse transit time (PTT), a concentration of a substance in blood and/or tissue, such as (arterial) blood oxygen saturation or glucose level.

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In an embodiment said analyzer is configured to compare spatial and/or optical properties of one or more data signals in one or more wavelength ranges to a respective template representing expected spatial and/or optical properties. Thus, based on this comparison it can be decided if the analyzed data signals correspond to a noisy signal or contain a useful vital sign information. The templates may be available from a statistical analysis of earlier analyzes or may be standardized. In an improved embodiment templates are used that are to a certain extent subject-specific. For instance, for a young person different templates may be used than for an old person, and for an ill person different templates may be used than for a healthy person.

In another embodiment said analyzer is configured to determine the main frequency components in the spectrum of said one or more data signals in said one or more wavelength ranges and to select one or more main frequency components in the expected range of the frequency of the vital sign to be determined. For instance, if the heart rate shall be determined as vital sign a frequency component in the expected range of the frequency of the heart rate is selected, i.e. in the range from about 0.5 to about 2 Hz. Preferably, as proposed in the further embodiment, the analyzer is configured to analyze the signal amplitude of the selected one or more main frequency components in the spectrum of said one or more data signals in said one or more wavelength ranges. Thus, the analysis is more precise since it focuses on the really interesting frequency component(s).

In a preferred embodiment said analyzer is configured to analyze the spatial distribution of the pulsatility in the wavelength range of visible and invisible light, in particular of green light. Generally, pulsatility is a measure of the variability of blood volume, equal to the difference between the peak systolic and minimum diastolic volumes divided by the mean volume during the cardiac cycle. It has been found that in the green channel the pulsatility is strongest on a forehead and cheeks of a person, and less strong on other parts of the face. This knowledge is evaluated according to this embodiment to improve the differentiation between noise and real signal.

In a similar embodiment said analyzer is configured to analyze the spatial distribution of the ratio of signal amplitudes in the wavelength range of red light versus the signal amplitudes in the wavelength range of infrared light. It has been found that the spatial distribution of the amplitude of the ratio Red/Infrared light at the same frequency component will be uniform over the face, which knowledge is evaluated according to this embodiment to improve the differentiation between noise and real signal.

Advantageously, said analyzer is configured to analyze the ratio of signal amplitudes between two different wavelength ranges, in particular between the wavelength range of green light and the wavelength range of red light. It has been found that the pulsatility of the data signals in the green channel is several times larger than in the red channel, which knowledge is evaluated according to this embodiment to improve the differentiation between noise and real signal.

Still further, in an embodiment said analyzer is configured to analyze the maximum range of signal amplitudes of the one or more data signals in various wavelength ranges and/or to analyze the temporal stability of signal amplitudes and/or of ratios of signal amplitudes of the one or more data signals in various wavelength ranges. Depending on the particular application this may further improve the result of the analysis.

In another embodiment said interface is configured to receive a data stream comprising a plurality of image frames of the subject acquired over a period of time. Thus, as mentioned above, the electromagnetic radiation is represented by a plurality of image frames obtained by an imaging unit, such as a camera.

Preferably, said interface is configured to receive a data stream comprising a plurality of image frames acquired with varying frame rate, and said analyzer is configured to select frequency components of the data signals for further analysis that are independent on the frame rate. Thus, other frequency components are interpreted as being caused by some source of noise, e.g. the camera, or as beating frequency of flickering illumination.

While the present invention generally works with data signals comprising a single data signal component representative of a single spectral portion (e.g. in the spectral range of green light), in an embodiment said data signals comprise at least two data signal components, wherein a first data signal component is representative of a first spectral portion, in particular a visible-light portion, and wherein a second data signal component is representative of a second indicative spectral portion, in particular an infrared portion. This idea makes use of the fact that a penetration depth of radiation which is dependent on blood absorption and tissue absorption is basically also dependent on the wavelength of incident radiation. Typically, infrared (or near-infrared) and red light penetrates deeper into the subject's tissue than visible light having shorter wavelengths. By way of example, the first spectral portion can be formed of a band or sub-band in the green portion of visible radiation.

As mentioned above the proposed system comprises an imaging unit, in particular a camera, for remotely detecting electromagnetic radiation reflected from the subject, in particular in one or two different spectral ranges. The imaging unit is particularly suited for remote monitoring applications. The imaging unit can comprise one or more imaging elements. For instance, the imaging unit can comprise an array of photodiodes or charge-coupled devices. According to an embodiment, the imaging unit comprises at least two groups of imaging elements each of which is configured for detecting a single one of the data signal components. According to another embodiment, the imaging unit can make use of a single group of imaging elements having a response characteristic allowing for a detection of data signal components. The imaging unit can be further configured for capturing a sequence of image frames alternatingly representing the data signal components.

In another preferred embodiment the proposed system further comprises a radiation source, in particular a light source, for directing electromagnetic radiation to the subject, for instance in one or two different spectral ranges. The radiation source can be embodied by a broadband illumination source and/or can make use of a single group or two or even more groups of radiation elements. However, the proposed system does not necessarily have to comprise a radiation source, but can also make use of ambient light sources which are not connected to the system.

According to a further aspect of the present invention a processor is presented for processing a received data stream derived from detected electromagnetic radiation reflected from a region of interest including a skin area of a subject, said processor being configured to receive said data stream comprising a data signal per skin pixel area of one or more skin pixels for a plurality of skin pixel areas of said region of interest, a data signal representing the detected electromagnetic radiation reflected from the respective skin pixel area over time, analyze spatial and/or optical properties of one or more data signals in one or more wavelength ranges, and determine a vital sign information signal of the subject based on the data signals of skin pixel areas within the skin area, wherein said determined spatial and/or optical properties are used for determining the vital sign information signal.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
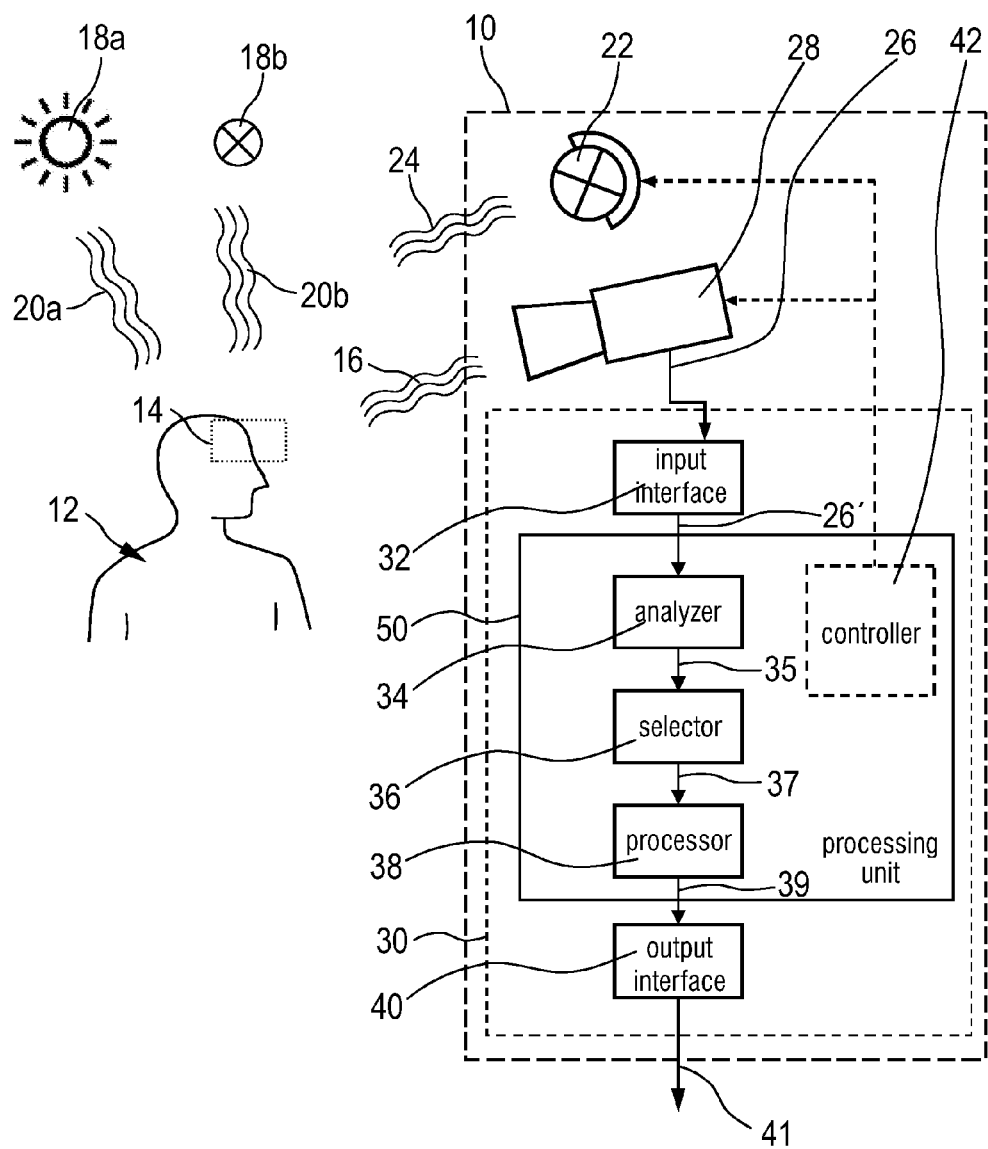
FIG. 1 shows a schematic diagram of a system in which a device according to the present invention is used.

FIG. 1 shows a schematic diagram of a system 10 in which a device 30 according to the present invention is used. The system 10 can be utilized for recording image frames representing a remote subject 12 or at least a portion 14 (a region of interest) of the subject 12 for remote PPG monitoring. The region of interest 14 comprises, by way of example, a forehead portion, a face portion or, more generally, one or more skin portions of the subject 12. The recorded data, for instance, a series of image frames, can be derived from electromagnetic radiation 16 reflected by the subject 12. Possibly, under certain conditions, at least part of the electromagnetic radiation could be emitted or transmitted by the subject 12 itself. Radiation transmission may occur when the subject 12 is exposed to strong illumination sources shining through the subject 12. Radiation emission may occur when infrared radiation caused by body heat is addressed and captured. However, for remote PPG applications, a huge portion of the electromagnetic radiation 16 to be captured can be considered radiation reflected by the subject 12. The subject 12 can be a human being or an animal, or, in general, a living being. Furthermore, the subject 12 can be considered a part of a human being highly indicative of a desired signal.

A source of radiation, such as sunlight 18a, an artificial radiation source 18b or a combination of several radiation sources, affects or impinges on the subject 12. The radiation sources 18a, 18b basically emit incident radiation 20a, 20b striking the subject 12. In addition, or in the alternative, the system 10 may also comprise or make use of an internal source 22 of electromagnetic radiation 24, which emits and directs incident radiation 24 to the subject 12 and which may also be part of the device 30 in an alternative embodiment. The internal source 22 of radiation 24 can be configured for directing radiation having defined characteristics to the subject 12, in particular radiation belonging to a defined spectral portion. Since in accordance with an embodiment of the invention, at least two distinct spectral portions are captured and processed, according to another aspect of this embodiment it is preferred that the internal source 22 of electromagnetic radiation 24 "matches" these spectral portions.

For extracting physiological information from the captured data, for instance, a sequence of image frames, radiation 16 from a defined part or portion of the subject 12, such as a the region of interest 14, is detected by an imaging unit 28. The imaging unit 28 can be embodied, by way of example, by an optical sensor means configured to capture information belonging to at least one spectral component of the electromagnetic radiation 16. In an embodiment, the imaging unit 28 is embodied by a camera or a set of cameras, such as a video camera (e.g. an RGB camera). The imaging unit 28 may also be part of the device 30 in an alternative embodiment.

Needless to say, the device 30 can also be adapted to process input signals, namely an input data stream 26, already recorded in advance and, in the meantime, stored or buffered. As indicated above, the electromagnetic radiation 16 can contain a continuous or discrete characteristic signal which can be highly indicative of at least one vital sign parameter 26, in the context of the present invention particularly the heart rate, respiration rate and/or blood oxygen saturation.

The device 30 for determining a vital sign of a subject according to the present invention comprises an (input) interface 32 for receiving the data stream 26 (from the imaging unit 28 or from a storage unit or buffer) derived from detected electromagnetic radiation 16 reflected (including emitted or transmitted radiation) from a region of interest 14 including a skin area of the subject 12. Said data stream 26 comprises a data signal per skin pixel for a plurality of skin pixel areas of one or more skin pixels (preferably for all skin pixel areas or even for all individual skin pixels) of said region of interest, wherein a data signal represents the detected electromagnetic radiation 16 reflected from the respective skin pixel area over time.

An analyzer 34 is provided for analyzing spatial and/or optical properties of one or more data signals in one or more wavelength ranges. Thus, information about the spatial and/or optical properties of the data signals is output from the analyzer 34 as will be explained in more detail below.

The device 30 further comprises a processor 36 for determining a vital sign information signal of the subject based on the data signals of skin pixel areas within the skin area and a post-processor 38 for determining the desired vital sign from said vital sign information signal. This way of processing the data signals is generally known in the art of remote PPG and shall thus not be explained in more detail here. Contrary to the known devices and methods, however, said determined spatial and/or optical properties are used by the processor 36 for determining the vital sign information signal and/or by the post-processor 38 for determining the desired vital sign.

Finally, an (output) interface 40 can be provided to which the determined vital sign 39 can be delivered, e.g. to provide output data 41 for further analysis and/or for display. Both interfaces 32, 40 can be embodied by the same (hardware) connectors.

In an embodiment a controller 42 is provided for selectively controlling at least one of the imaging unit 28 and the radiation source 22.

The analyzer 34, the processor 36 and the post-processor 38 (and, if provided, the controller 42) may be implemented by a common processing unit 50 which can be considered as a computing device, or at least, part of a computing device driven by respective logic commands (program code) so as to provide for desired data processing. The processing unit 50 may comprise several components or units which are addressed in the following. It should be understood that each component or unit of the processing unit 50 can be implemented virtually or discretely. For instance, the processing unit 50 may comprise a number of processors, such as multi-core processors or single-core processors. At least one processor can be utilized by the processing unit 50. Each of the processors can be configured as a standard processor (e.g., central processing unit) or as a special purpose processor (e.g., graphics processor). Hence, the processing unit 50 can be suitably operated so as to distribute several tasks of data processing to adequate processors.

The processing unit 50 as well as the interfaces 32, 40 can be embodied in a common processing apparatus or housing, generally representing the proposed device 30. The imaging unit 28 and the radiation source 22 are generally external elements, but may also be integrated into the device 30, e.g. with a common housing with the other elements of the device 30.

In the following, details of the present invention and of preferred embodiments shall be explained.

It is often assumed that noise is a non-periodic signal and that the vital sign (e.g. heartbeat or respiratory motion) is the only periodic signal. This, however, is not always true, and the method of just searching for a periodic signal does not always lead to reliable vital sign detection.

The proposed device and method are more efficient in distinguishing a real periodic vital sign information signal (e.g. a pulse signal) from noise with similar temporal characteristics. The improvement of the extracted vital sign is particularly based on the analysis of the optical and/or spatial properties of a remote PPG signal used for extraction of a desired vital sign.

In a preferred embodiment the imaging unit 28 comprises a camera having at least two color channels (e.g. red and green of RGB camera) to differentiate a real PPG signal from other repetitive signals with frequencies and amplitude range similar to the PPG signal. Different principles may be used to distinguish a real pulse signal from a noise signal. Spatial properties take account of the distribution of the PPG amplitude over one or more skin pixel areas. Optical properties take account of the ratio of PPG amplitudes in color channels depending on a wavelength, the maximum range of amplitudes of PPG signals in various color channels and/or the temporal stability of amplitudes of PPG signals in various color channels.

Spatial properties are evaluated since the amplitude of the PPG signal is not the same over a face of a person. Although the exact pattern of PPG imaging (spatial map of amplitude of PPG signal) is different for each person, there are common features, which can be used to distinguish a PPG signal acquired from a face and a noise signal. For instance, the pulsatility of PPG in the green channel is strongest on a forehead and slightly less on cheeks of a person. At the same time, the spatial distribution of the amplitude of the ratio red/infrared at the same frequency will be uniform over the face. In both cases, an imaging of green PPG signal and/or PPG imaging of red/infrared would not coincide with a spatial distribution of intensity gradient. Otherwise, in case an AC/DC amplitude of a repetitive signal is spatially distributed equally over the face, or strongly correlated with illumination gradient, then most probably this signal is caused by changes of illumination or other factors not related to a heartbeat.

Figure 2:
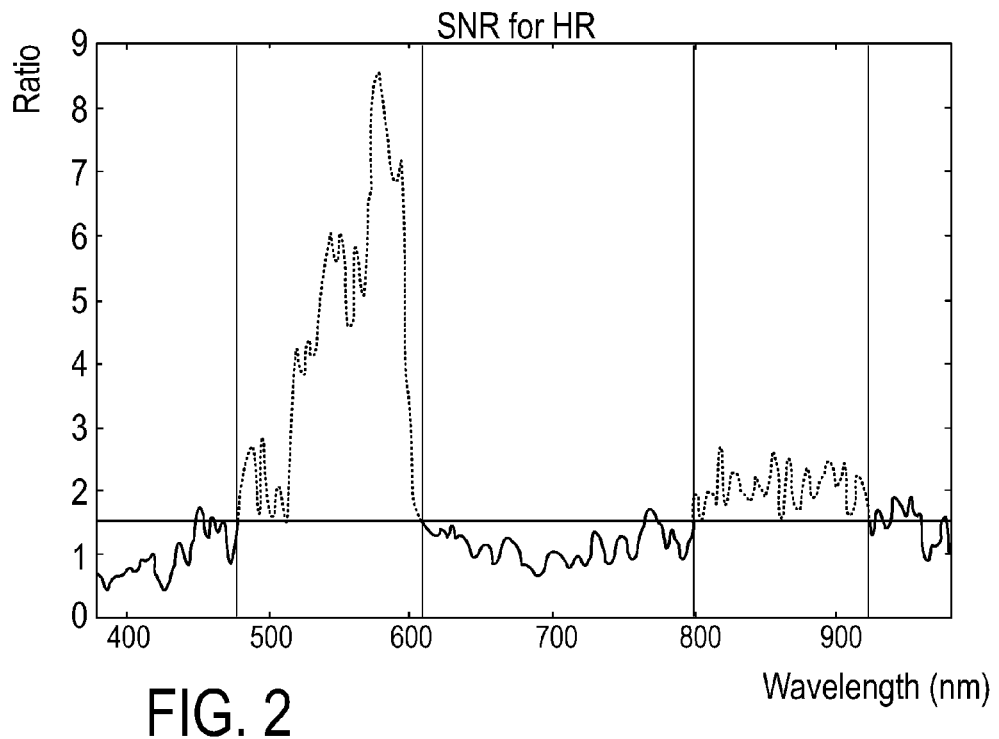
FIG. 2 shows a diagram illustrating the dependence of the PPG pulsatility on the wavelength of the reflected light.

Optical properties are evaluated since the PPG signal has different normalized amplitudes (pulsatility) in various color channels. FIG. 2 shows the dependence of the PPG pulsatility on the wavelength of the reflected light. It has been proven that the pulsatility of the PPG signal in the green channel (550-600 nm) is several times larger than in the red channel (around 700 nm). This principle is used in an embodiment to differentiate a real PPG signal from noise, which would have a distribution of amplitudes in color channels different from the one shown on FIG. 2.

An even higher degree of certainty that a periodic signal is induced by cardiovascular activity can be reached by benefiting from two additional recognitions. First, the range of physiological amplitudes for the respective wavelength bands is used in an embodiment. Second, the relationship between red and infrared (IR) is typically much stronger (more reliable) than the relationship between green and one of the other wavelengths as visualized in FIG. 3 for 247 recordings on the foreheads of 47 different individuals. Both the physiological range of the PPG amplitudes and their relative strengths (and reliabilities) can be determined experimentally.

Figure 3:
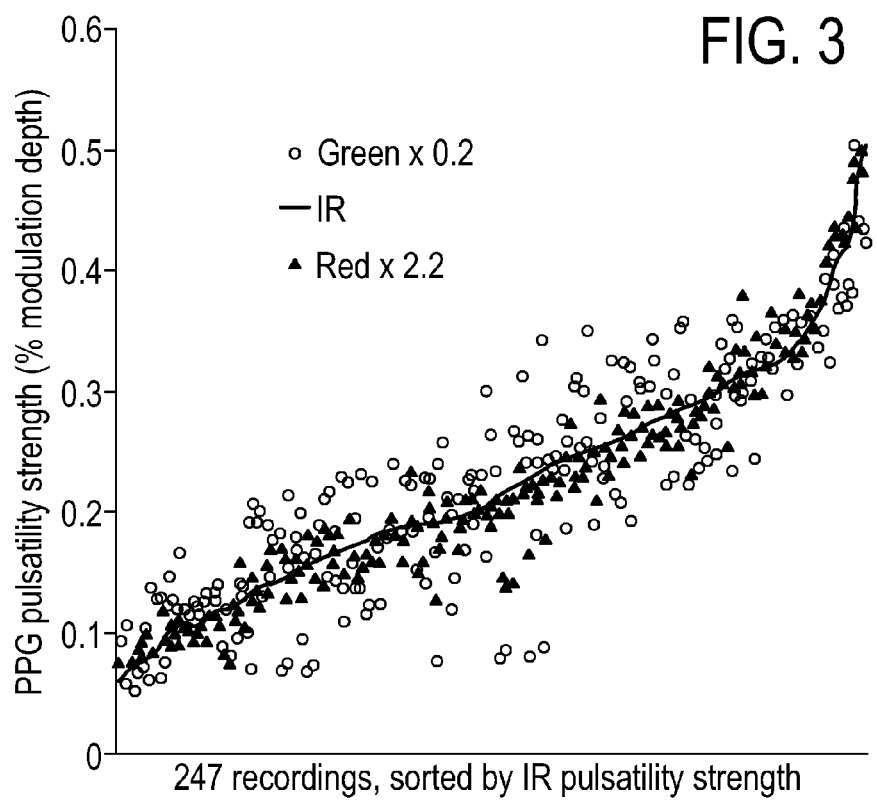
FIG. 3 shows a diagram of the amplitudes of green, red and IR illustrate the physiologic ranges of the PPG amplitudes at green, red and IR, respectively.

FIG. 3 particularly shows that the amplitudes of green, red and IR illustrate the physiologic ranges of the PPG amplitudes (0.7-1.5%, 0.07-0.13% and 0.15-0.28%) at green, red and IR, respectively. It also shows that the relationship between red and IR is quite steady (they differ by a factor of about 2.2) and also more reliable than that between green and IR and should thus have a larger statistical weight to determine if a signal is a true PPG signal or not.

The relative amplitudes between the wavelength bands may differ slightly for different facial areas such as the cheek, nose, forehead etc. Such statistical differences are also used to enhance reliability in an embodiment.

Figure 4:
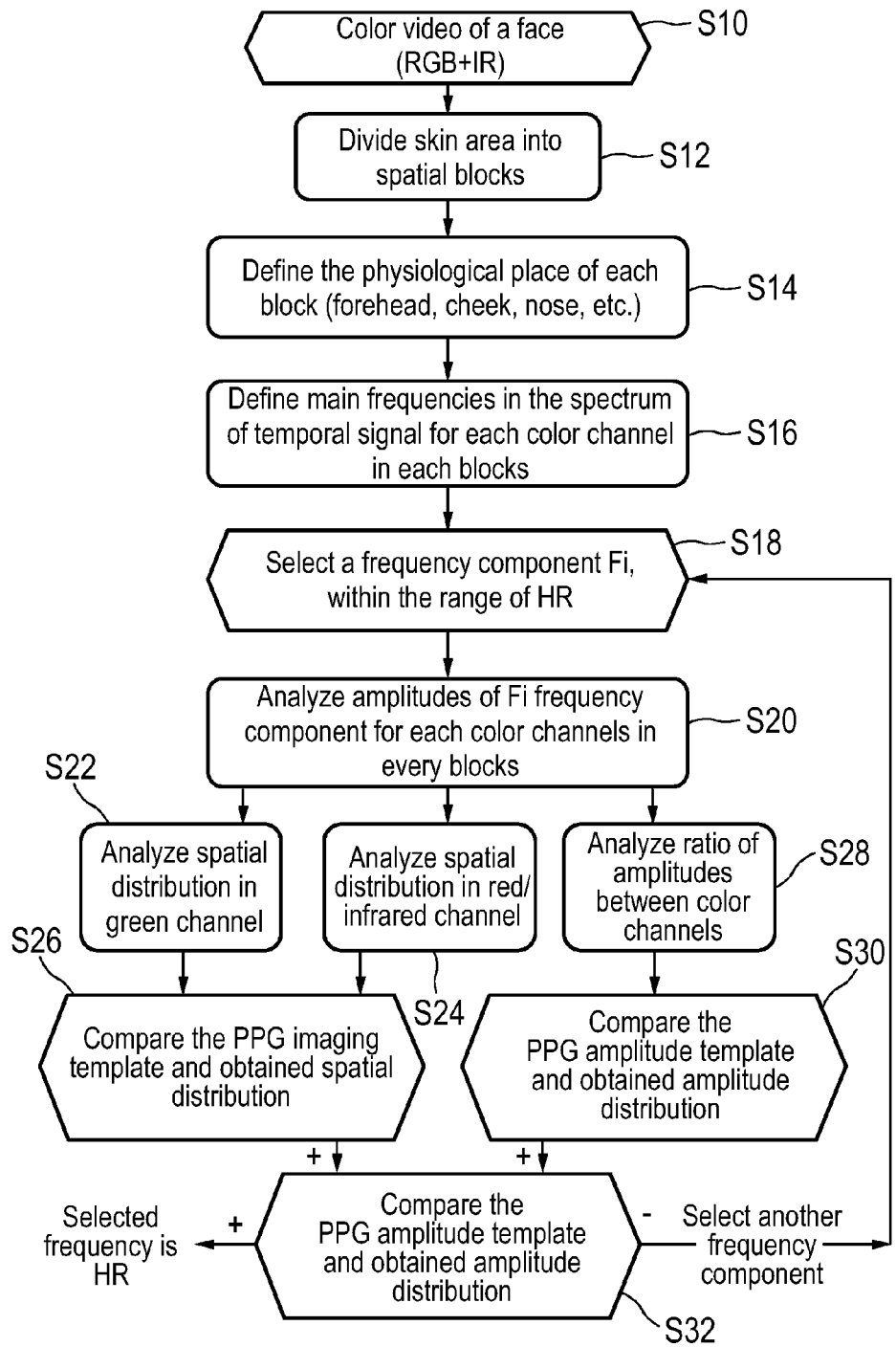
FIG. 4 shows a flowchart of an embodiment of a method according to the present invention.

A flowchart illustrating the steps of an exemplary embodiment of the proposed method is depicted in FIG. 4. The example explained with reference to FIG. 4 assumes the availability of RGB and IR channels. It is further assumed that a simple pre-processing is applied (not shown) during the extraction of temporal AC/DC signals to normalise for changes of intensity of ambient illumination.

In a first step S10 a skin area of a face is detected. The detected skin area is divided into spatial blocks (S12) and the physiological place of each block (forehead, cheek, nose, etc.) is defined (S14). In case of a motion of the face area, motion compensation is applied (not shown) to track each spatial block. After that, the frequency analysis of temporal (AC/DC) signals inside each block is performed. In particular, main frequencies in the spectrum of the temporal (PPG) signal for each color channel in each block are defined (S16) and the frequency components within the range of the expected HR (e.g. 0.5-2 Hz) are selected (S18). After that, each frequency component is analyzed iteratively.

In the analysis the amplitudes of the respective frequency component analyzed in the respective iteration are analyzed for each color channel in each block (S20). One or more kinds of analysis are generally performed. In one kind the ratio of amplitudes in color channels (preferably green and red/infrared) for this particular frequency component is analyzed (S22, S24) and compared with the expected distribution of the PPG signal amplitude (S26). In another kind (preferably in parallel) the spatial distribution of the puslatility corresponding to the currently selected frequency component is analyzed (S28), and compared with the expected template of PPG imaging (S30).

If both the distribution of amplitudes between color channels and the spatial distribution of amplitudes are correlated with templates of spatial and amplitude distribution of PPG signal (S32), this is interpreted such that the selected frequency corresponds to the heartrate. Otherwise, another frequency component from the bandpassed spectrum is selected (S18) and another iteration of the steps S20 to S32 is carried out.

Thus, in summary, a device and method for detection and analysis of remote photoplethysmography (R-PPG) signals are provided using a camera unit with at least two color wavelength measure temporal signals (PPG signals) from a skin area, a unit to analyze the spatial distribution of amplitudes of temporal signals in each color channel and a unit to analyze the ratio of amplitudes of temporal signals in each color channel. In an embodiment a unit is provided for comparison of spatial distribution of amplitude of temporal signals versus pre-defined spatial template. In another embodiment a unit is provided for comparison of ratio of amplitudes of the same temporal signal in different color channels versus pre-defined template of amplitude distribution. In another embodiment a unit is provided for analysis of temporal stability of ratio of PPG amplitudes in red over infrared channels versus the ratio of PPG amplitudes in red over green or infrared over green channels. In another embodiment a unit is provided for analysis of spatial uniformity of ratio of PPG amplitudes in red over infrared channels versus the ratio of PPG amplitudes in red over green channels.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art.

Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for determining a vital sign of a subject comprising:
    an interface configured to receive a data stream derived from detected electromagnetic radiation reflected from a region of interest including a plurality of skin areas of the subject irradiated by ambient light, said data stream comprising a data signal per skin pixel area of one or more skin pixels for each of the plurality of skin areas of said region of interest, a data signal representing the detected electromagnetic radiation reflected from the respective skin pixel area over time,
    an analyzer configured to analyze spatial and optical properties of the data signals in a plurality of wavelength ranges,
    a processor configured to differentiate between a vital sign information signal of the subject and background noise based on the data signals of skin pixel areas within the plurality of skin areas, and
    a post-processor configured to determine the desired vital sign from said vital sign information signal.

2. The device as claimed in claim 1, wherein said analyzer is further configured to:
    compare wavelength properties of the data signals in the plurality of skin areas to a respective template representing expected wavelength differences and similarities among the skin areas.

3. The device as claimed in claim 2,
    wherein said analyzer is configured to determine a spectrum of frequency components of said data signals from ones of the skin areas and compare the spectrums with an expected spectrum of the frequency components of the vital sign to be determined.

4. The device as claimed in claim 1, wherein said analyzer is further configured to:
    determine a spectrum of frequency components of said data signals from ones of the skin areas and compare the spectrums with an expected spectrum of the frequency components of the vital sign to be determined.

5. The device as claimed in claim 1,
    wherein said interface is configured to receive a data stream comprising a plurality of image frames of the subject acquired over a period of time.

6. A device for determining a vital sign of a subject comprising:
    an interface configured to receive a data stream derived from a two dimensional color imager of at least one skin area of the subject, said data stream comprising a data signal for each of a plurality of skin pixels of the skin area representing detected electromagnetic radiation reflected from the skin area over time;
    one or more processors configured to:
        select main frequency components in a spectrum of the data signal, in wavelength ranges,
        determine amplitudes of the selected main frequency components in the spectrum of said data signals in said wavelength ranges,
        compare the determined amplitudes with a distribution of the amplitudes of the main frequency components of a template characteristic of photoplethysmorgraphy signals;
        if the determined amplitudes correspond to the template, using the data signals to determine the vital sign.

7. The device as claimed in claim 6, wherein the one or more processors are further configured to:
    determine ratios of signal amplitudes between different wavelength ranges of the main frequency components; and
    comparing the ratios with the template.

8. The device as claimed in claim 6, wherein the one or more processors are further configured to:
    analyze a maximum range of the signal amplitudes in the wavelength ranges.

9. The device as claimed in claim 6, wherein the one or more processors are further configured to:
    analyze a temporal stability of the signal amplitudes of the data signals in the wavelength ranges.

10. The device as claimed in claim 6, wherein the one or more processors are further configured to:
    analyze a spectral distribution of amplitudes of data signal components in each of a plurality of corresponding color channels in each of the skin areas and compare the spectral distributions with a predefined spectral template, and in response to the spatial and spectral distributions matching the predefined spatial and spectral templates, using the data stream to determine the vital sign.

11. A device for determining a vital sign of a subject comprising:
    an interface configured to receive a data stream derived from detected electromagnetic radiation reflected from a region of interest including a plurality of skin areas of the subject, said data stream comprising a data signal per skin pixel area of a plurality of skin pixels of each of the plurality of skin areas of said region of interest, a data signal representing the detected electromagnetic radiation reflected from the respective skin pixel area over time;
    an analyzer configured to analyze a spatial distribution of a pulsatility in a wavelength range of visible and invisible light, the analyzer including one or more processors configured to:
    analyze a spatial distribution of amplitudes of data signal components in each of a plurality of corresponding color channels in the plurality of skin areas,
    compare the spatial distribution with a predefined spatial template,
    in response to the spatial distribution matching the template, using the data stream to determine the vital sign.

12. The device as claimed in claim 11, wherein said one or more processors are configured to:
    analyze the spatial distribution of a ratio of signal amplitudes in the plurality of color channels and compare the spatial distribution of the ratios with the template.

13. The device as claimed in claim 11, wherein the one or more processors are further configured to:
    analyze a spatial distribution of the amplitudes of the data signal components in each of a plurality of corresponding color channels in a plurality of skin areas and compare the spatial distribution with a predefined spatial template, and determining the vital sign in response to both the determined amplitudes corresponding to the photoplethysmorgraphy template and the spatial distribution corresponding the predefined spatial template.

14. A method for determining a vital sign of a subject comprising:
receiving a data stream derived from detected electromagnetic radiation reflected from a region of interest including a skin area of the subject, said data stream comprising a data signal per skin pixel area of skin pixels for a plurality of skin areas in said region of interest, a data signal representing the detected electromagnetic radiation reflected from the respective skin pixel over time,
analyzing spatial and optical properties of the data signals in a plurality of wavelength ranges to differentiate between the data signals corresponding to vital sign information and the data signals corresponding to the noise, and,
determining the vital sign from the data signals corresponding to the vital sign information signal and disregarding the data signals corresponding to the noise.

15. A computer readable non-transitory medium having instructions stored thereon which, when carried out on a computer, cause the computer to perform the steps of the method as claimed in claim 14.

16. The method as claimed in claim 14, wherein analyzing the spatial and optical properties of the data signals includes:
determine amplitudes of selected components in the plurality of wavelength ranges in each of a plurality of color channels of the plurality of blocks to generate a spatial distribution and comparing the spatial distribution with a spatial distribution template,
analyzing amplitudes of selected components in each of the color channels within each of the skin areas to obtain an amplitude distribution within each of the skin areas and comparing the amplitude distribution with a predetermined amplitude template; and
wherein the vital sign is determined when the spatial distribution matches the spatial template and the amplitude distribution matches the amplitude template.

17. A system for determining a vital sign of a subject comprising:
an imaging unit configured to detect electromagnetic radiation reflected from a region of interest including a skin area of the subject to obtain a data stream, said data stream comprising a data signal per skin pixel for a plurality of skin areas of said region of interest, a data signal representing the detected electromagnetic radiation reflected from the respective skin pixel over time, and
a processing device configured to:
receive said data stream,
analyze the data stream for distribution of frequency components from the one or more skin areas to determine frequency components distribution,
based on the frequency component distribution, determining whether the data stream is characteristic of the vital sign or noise,
if the data stream is characteristic of the vital sign, determining the vital sign.

18. A processor for processing a received data stream derived from detected electromagnetic radiation reflected from a region of interest including a skin area of a subject, said processor being configured to:
receive said data stream comprising a data signal per skin pixel area of skin pixels for each of a plurality of skin area blocks in said region of interest, a data signal representing the detected electromagnetic radiation reflected from the respective skin pixel over time,
define main frequencies in a spectrum of the data signals for each of a plurality of color channels in each block,
select a component of the main frequencies within a range of the vital sign,
analyze amplitudes of the selected components in each of the color channels of the blocks,
analyze a spatial distribution of the selected component among the blocks in at least one selected color channel,
compare the spatial distribution with a photoplethysmorgraphy imaging template,
analyze a ratio of amplitudes between color channels for the selected component with each block to obtain an amplitude distribution,
compare the amplitude distribution with a photoplethysmorgraphy amplitude template,
if both the spatial distribution matches the imaging template and the amplitude distribution matches the amplitude template, outputting the selected component as the vital signal, and
if one of the spatial and amplitude distributions fail to match the respective template, selecting different component of the main frequencies and repeating the analyzing and comparing operations.

* * * * *